United States Patent [19]

Rigler

[11] Patent Number: 5,116,125
[45] Date of Patent: May 26, 1992

[54] FERTILITY ANALYZER

[75] Inventor: Rudolf Rigler, Danderyd, Switzerland

[73] Assignee: Biophos Medical AB, Stockholm, Sweden

[21] Appl. No.: 605,092

[22] Filed: Oct. 31, 1990

[51] Int. Cl.$^5$ .................... G01N 15/02; G01N 21/00
[52] U.S. Cl. ..................... 356/343; 356/336
[58] Field of Search ................ 356/337–343, 356/244, 440, 442, 73, 335, 336, 369; 250/222.2, 574

[56] References Cited

U.S. PATENT DOCUMENTS

| | | | |
|---|---|---|---|
| 3,819,270 | 6/1974 | Hirschfeld | 356/343 |
| 4,601,578 | 7/1986 | Woolhouse et al. | 356/338 |
| 4,648,715 | 3/1987 | Ford et al. | 356/343 |
| 4,676,641 | 6/1987 | Bott | 356/338 |
| 4,896,966 | 1/1990 | Boisseau et al. | 356/244 |
| 4,896,967 | 1/1990 | Douglas-Hamilton et al. | 356/244 |

OTHER PUBLICATIONS

Rotational and Translational Swimming of Human Spermatozoa: A Dynamic Laser Light Scattering Sturdy, Rigler & Thyberg (1984).
Translational and Rotational Swimming of Human Spermatozoa: Maxwell Speed Distribution in the Analysis of Dynamic Laser Light Scattering, by Rigler & Thyberg (1986).

Primary Examiner—Richard A. Rosenberger
Assistant Examiner—Hoa Pham
Attorney, Agent, or Firm—Young & Thompson

[57] ABSTRACT

A fertility analyzer includes a laser beam impinging on a sperm sample in a capiliary, a first optical system including at least a first lens focusing the laser beam in the sample, and a second optical system including at least a second lens, a first diaphragm determining the volume element of the sample to be monitored, a second diaphragm determining the space angle of scattered light and a light intensity detector. A signal processing device stores the signals from the light detector during a predetermined time separately for beams outgoing from the sperm sample in at least two chosen directions and computes at least two features having relation to the fertility of the sperm sample. A separator included in the combination of the first and second optical systems sorts out a determinable small section of the beam outgoing from the sperm sample in a direction lying in a plane approximately parallel to a plane including the capillary.

10 Claims, 4 Drawing Sheets

FERTILITY ANALYZER

BACKGROUND OF THE INVENTION

This invention relates to a fertility analyzer.

Analyzing mobility and number of spermatozoa is of importance in order to judge the spermatozoa fertility features. Most often nowadays video registration of the spermatozoa movements is used together with computer based analyzing of individual trajectories.

According to a known method, discussed in U.S. Pat. No. 4,601,578, a sperm sample is illuminated by a laser beam and a spectral analysis is made of the laser light scattered from the sample. The signal is transferred through filters and integrators and an output pulse is given each time an integrator is saturated. The saturation pulses are counted. The sample is illuminated by an approximately collimated laser light. The light scattered from the sample is transferred to a detector through a semicircular aperture in a disc and a focusing lens. By this known method only an unspecified sperm motility is detected just to give a general idea of the percentage living sperms in a sample.

However, the fertility is determined by a lot of different features of the spermatozoa, of which the most essential are the translational speed and the rotational frequency, and a quite specific sperm motility value is the ratio between the translational speed and the rotational frequency.

A few years ago a new method was developed by a team in which the inventor of this invention was a participant. According to that method the spermatozoa mobility is measured by analyzing light, which is scattered or emitted when the spermatozoa are illuminated with a laser beam. This method is described in the articles "Rotational and Translational Swimming of Human Spermatozoa: A Dynamic Laser Light Scattering Study", by Rigler, R. & Thyberg, P., Cytometry 5:327-332 (1984) and "Translational and Rotational Swimming of Human Spermatozoa: Maxwell Speed Distribution in the Analysis of Dynamic Laser Light Scattering", by Rigler, R. & Thyberg, P., In "Laser", ed G. Galetti, p. 105, Monduzzi Editore. Bologna (1986). According to these articles, the disclosure of which is incorporated herein by reference and which are attached to the specification as an APPENDIX, the mobility of the spermatozoa gives rise to fluctuations of the scattered light with a frequency related to the translational speed and the rotational frequency of the spermatozoa. The translational speed (in μm/sec) and the rotational frequency (in Hz) for an extensive population of spermatozoa are determined by computer aided Fourier transform analysis of the fluctuation spectrum of the spermatozoa using the light emitted in two directions from a spermatozoa sample illuminated by a laser beam.

The experimental set-up for the measurement of polarized and depolarized dynamic laser light scattering at various angles in a plane perpendicular to the extension of a tube containing the spermatozoa sample shown in the articles mentioned above has not been adapted for clinical analyses. The experimental set-up shown in FIG. 1 in the articles includes an analysing arrangement including many components, and the whole arrangement is moved along a circular path around the sample. The arrangement is thus quite clumsy including heavy parts to be moved.

Therefore, the main object of the invention is to provide an apparatus based on the theories described in the articles but adapted to be a complete instrument easy to handle.

SUMMARY OF THE INVENTION

In accordance with the principles of the present invention there is provided a fertility analyzer, including a) a laser beam impinging on a sperm sample in a capillary, b) a first optical means including at least a first lens means focusing the laser beam in the sample, c) a second optical means including at least a second lens means, a first diaphragm means determining the area or region of the sample to be monitored, a second diaphragm means determining the space angle of scattered light and a light intensity detecting means, d) a signal processing device storing the signals from the light detecting means during a predetermined time separately for beams outgoing from the sperm sample in at least two chosen directions, computing at least two features having relation to the fertility of the sperm sample, e) a separating means included in the combination of the first and second optical means sorting out a determinable small section of the beam outgoing from the sperm sample in a direction lying in a plane having space symmetry in relation to the capillary.

The separating means may include the second lens means being divided in a first part providing a collimated light beam and a second part providing the focusing of the beam on the detecting means and the second diaphragm means being provided in the collimated light beam between the first and second part of the second lens means and having a diaphragm opening disposable along a line lying in the plane, and the light detecting means includes a detector element placed on the optical axis of the second lens means.

The second diaphragm means may include one disposable part having several diaphragm openings provided along its disposal direction and one stationary part having openings adapted to the diaphragm openings such that it for every chosable position of the first part all diaphragm openings except one are covered for the beam outgoing from the sperm sample.

The separating means may instead include the second lens means being divided in a first and a second part, the first part providing an image of the sample between the first and the second part and the diaphragm means includes a diaphragm opening provided at the image, and the light detecting means includes an array of detector elements provided along a line parallel to the capillary, each detector element providing the second diaphragm for itself.

The separating means may instead include a mirror in the first optical means provided oblique to the beam path of the beam coming from the laser. This mirror deflects the beam path impinging an the first lens means parallel to the optical axis of the first lens means along a line perpendicular to the capillary, and the light detecting means is a single detector element and the first and second diaphragm means in the second optical means are diaphragm openings disposed between the second lens means and the detector element.

A cup formed means of glass containing a liquid is thermo regulated to a predetermined temperature and having approximately the same refractive index as the capillary at this temperature, in which cup formed means the capillary is seated.

Preferably, at least one opening in the second diaphragm means is arrangeable to have a size transmitting a substantial number of coherence areas, and the signal processing device is adapted to compute the number of sperms in the volume corresponding to the examined area by aid of autocorrelation of a series of signal samples recorded during a predetermined time having the large sized diaphragm area in a predetermined position.

The signal processing device preferably controls the separating means in accordance with a measuring program to automatically in a prescribed order provide prechosen space areas of the beam outgoing from the sperm sample for recording of signal samples during prescribed times.

Other objects and advantages of the invention will be apparent from the following description, the accompanying drawings and the appended claims.

DESCRIPTION OF THE PREFERRED EMBODIMENTS

Figure 1:
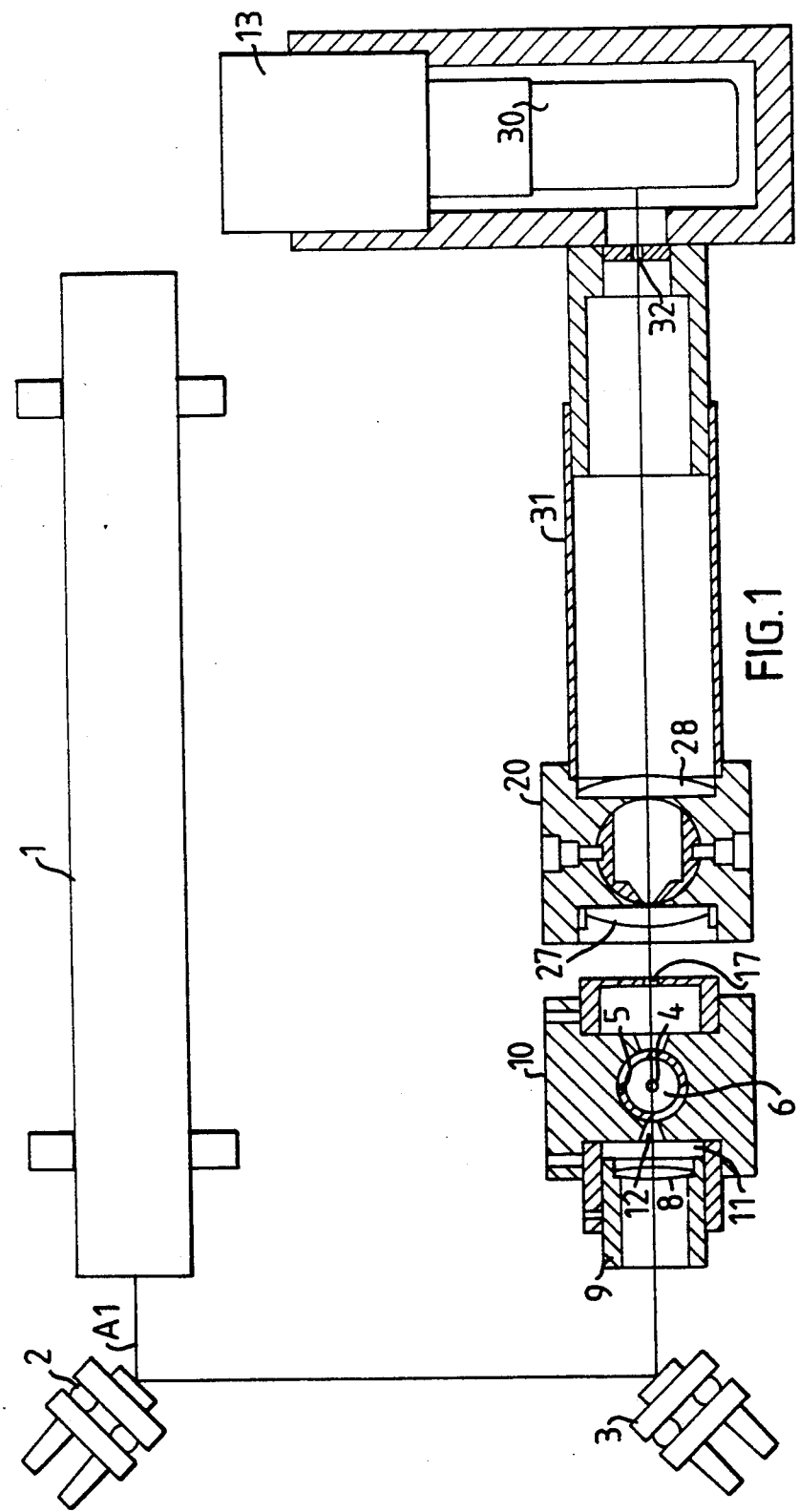
FIG. 1 shows a view from above of an embodiment of the instrument according to the invention.
Figure 2:
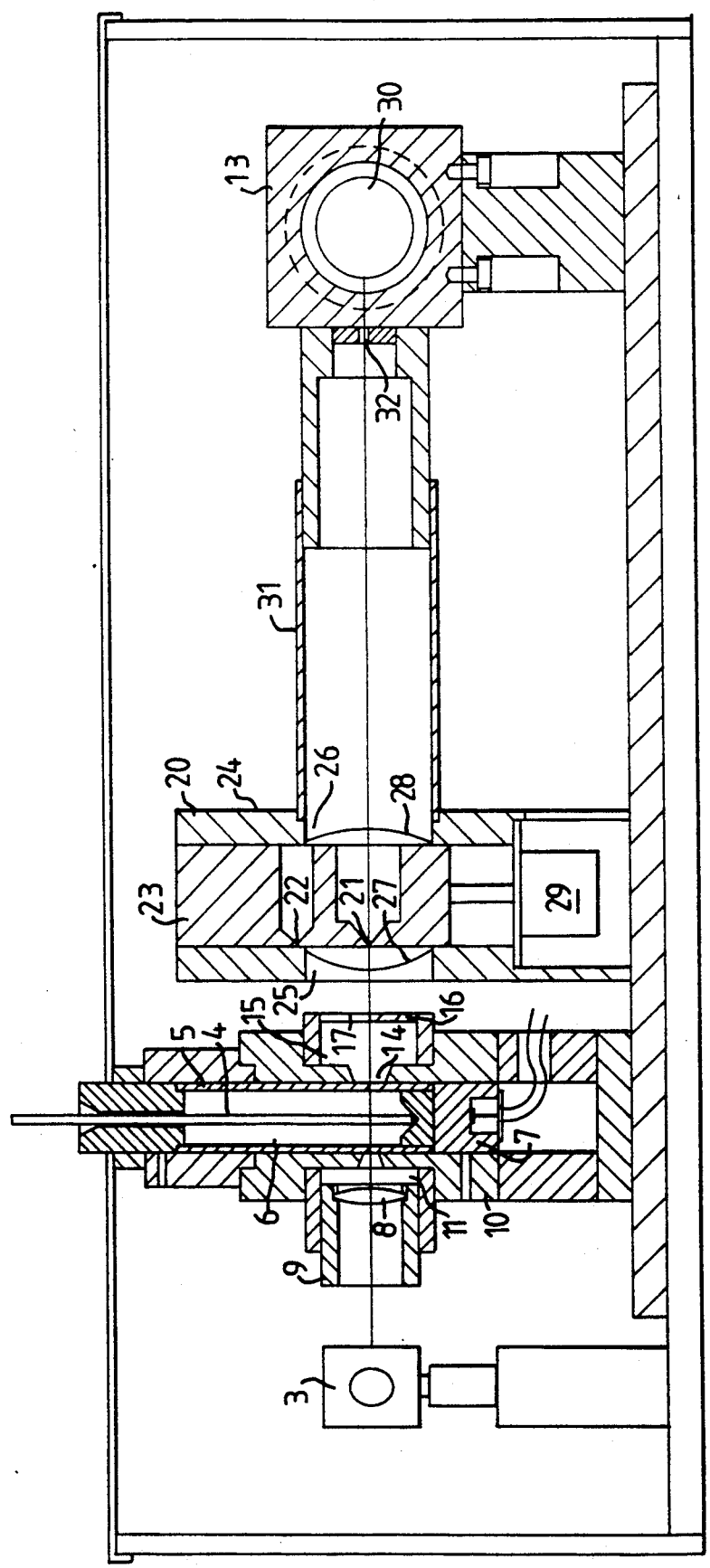
FIG. 2 shows a side view of the instrument shown in FIG. 1.

In the set-up shown in FIGS. 1 and 2, a laser 1, for instance a HeNe laser, emits a laser beam Al. The laser beam Al is bent 180° by two mirrors 2 and 3 each bending it 90°, i.e. being placed 45° to the beam path. The sperm sample is placed in a glass capillary 4. The glass capillary 4 is contained centrally in a larger thermostated glass tube 5 filled with a fluid 6, the refraction index of which is practically the same as the refractive index of the glass material of the glass capillary 4, at least at the operating temperature, in order to prevent stationary local reflections. The glass tube 5 is situated in a housing 10 and is warmed by a heater (not shown), and a temperature sensor T is provided in a thermally conducting block 7 in thermal contact with the tube 5. The heater is thermo regulated by aid of the sensor T in a way well known in the art and therefore not further described. The specific mechanical construction of the housing is not a part of the invention in itself and will therefore not be described in detail. The essential is that the liquid surrounding the capillary 4 is kept at a constant temperature, preferably slightly below 37° C.

The laser beam is focused on the sperm sample by a lens 8 placed quite near to the tube 5 in a tube 9 having a black, lustre-less inner surface and provided in the wall of the housing 10 perpendicular to the tube 5. The beam is transferred from the lens 8 to the capillary 4 through a filtering plate 11, a conical opening 12 having its wider end towards the plate 11, the wall of the tube 5 and the fluid 6. The filtering plate 11 is preferably a passband filter transmitting a narrow band around the laser wavelength.

The light beam is scattered by the sperms in the capillary 4. Light spread at different angles in an angular region in a plane containing the capillary axis and the optical axis of the laser beam is to be examined. This scattering plane has been chosen in the embodiment shown in FIGS. 1 and 2 because the capillary 4 should preferably be placed vertically extended and the instrument can be made very compact occupying as little area as possible horizontally if all moving parts are to be moved in a vertical direction. However, the beam scattered from the sample in a plane perpendicular to the capillary could be indicated instead (not shown). The essential is that a plane having space symmetry is chosen, i.e. a plane including the capillary axis or a plane perpendicular to it.

In the embodiment shown in FIGS. 1 and 2, the light from the capillary 4 is transferred to a detector device 13, preferably including a one-photon detector, through firstly a conical opening 14 in the housing 10 open to a cylindrical short tube 15 having black, lustre-less innerwalls and being closed at its outer end by a plate 16 having an opening 17 elongated in the same direction as the capillary 4 and secondly a diaphragm device 20 having two pinholes 21 and 22 provided in a column 23 displacable in the direction of the capillary 4 within a housing 24 having a cylindrical opening 25 facing the capillary 4 and another cylindrical opening 26 in the wall just opposite the wall with the opening 25, the diaphragm device cooperating with the opening 17 in such a way that only one opening at a time is opened for the light beam outgoing from the sample. A lens 27 is provided in the opening 25 and a lens 28 in the opening 26. A first polarizer may be placed at the open end of the tube 9 in case of measurement with polarized light, and then a second polarizer could be placed at the output of the diaphragm device 20.

The column 23 with the pinholes is positioned by a stepping motor 29 which is controlled by a computer (not shown), such as a PC (personal computer), which also is connected to the detector device 13. The intensity of the scattered laser light is measured at various angles by moving the pinholes. The computer performs data sampling and analysis.

The measured light scattered in predetermined angular directions from the sample is measured by single photon counting in a detector 30 in the device 13. A closed path including a tube means 31 having a black, lustreless innerwall is situated between the diaphragm device 20 and the detector 30 in order to minimize the influence of possible stray light. The tube means 31 is provided by two telescoping tubes in order to make it possible to adjust the distance between the devices 20 and 13. The tube means 31 is not absolutely necessary. A pinhole diaphragm 32 is provided in front of the detector 30 at the focus of the lens 28. Since the lens 27 is focused on the capillary 4, then an image of the pinhole 32 is provided on the capillary. As will be further explained below the pinhole 32 determines the area or region of the sample to be examined, and the diaphragm device 20 determines the coherence area of the scattered light.

Intensity fluctuations caused by the sperm motion are stored in a memory in the computer. A fast processor is used to calculate an autocorrelation function in the way described in the articles of the attached APPENDIX and to display this function on a screen. Translational velocities and rotational frequences as well as distribution functions are calculated from the autocorrelation functions measured at different angles. In order to separate the translational velocity v from the rotational frequency f the coherent light scattered in two different angular directions is measured, preferably 2° and 30°. The angular directions for each measurement are provided by aids of the diaphragm device 20 in a way which will be described further below.

In the embodiment shown in FIGS. 1 and 2 the detector 30 is a one-photon detector. The signals from the detector 30 are transferred to the signal processor, which calculates the autocorrelation and stores it in the memory connected to the processor.

The translation speed v must be separated from the rotational frequency f. In order to achieve this the coherent laser light scattered at different angles is measured. A volume element has to be defined in order to achieve coherently scattered photones. The best way to do this is to make a reduced image of a pinhole on the sample, such as an image of the pinhole 32 on the capillary 4 in the embodiment shown in FIGS. 1 and 2. Another way to achieve this is to have an aperture diaphragm which determines the observed space angle and hence the coherence area, such as by the pinholes 21 or 22 in the embodiment shown in FIGS. 1 and 2.

Figure 3:
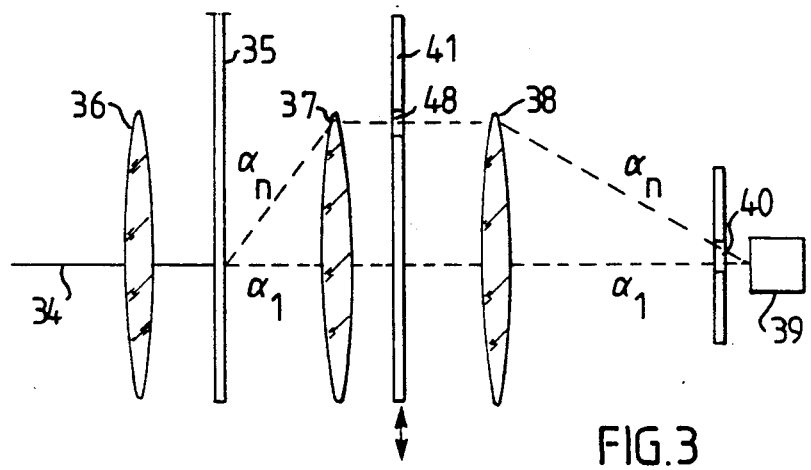
FIG. 3 shows schematically the beam path in a variant of the embodiment shown in FIGS. 1 and 2.
Figure 5:
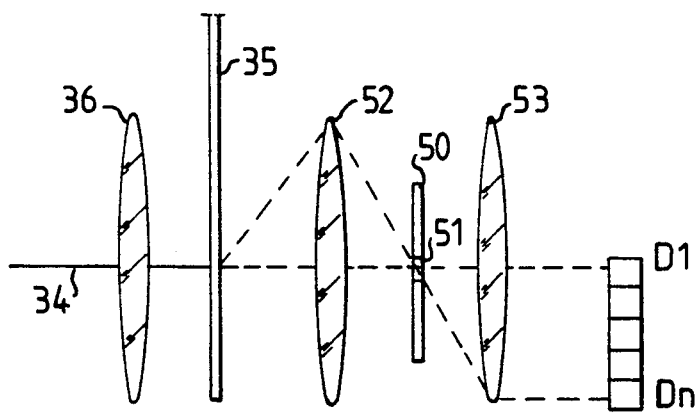
FIG. 5 shows schematically the beam path in a second embodiment of the instrument according to the invention.
Figure 6:
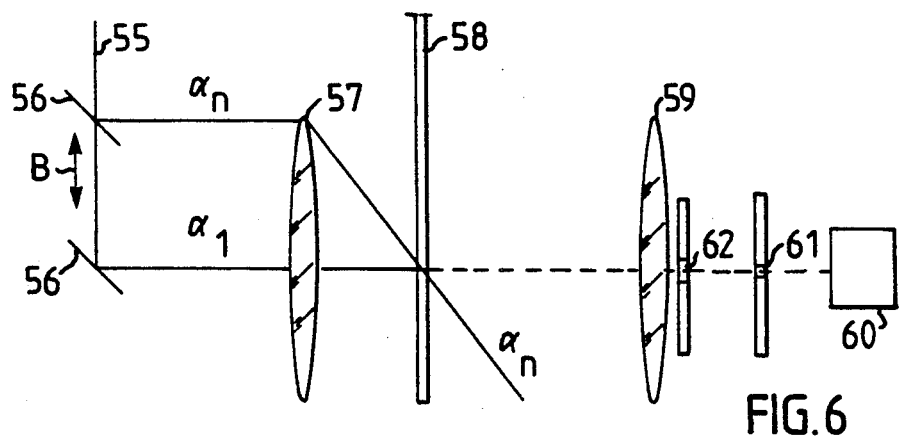
FIG. 6 shows schematically the beam path in a third embodiment of the instrument according to the invention.

Three embodiments to do this are schematically illustrated in FIGS. 3, 5 and 6.

The embodiment shown in FIG. 3 is a variant of the one illustrated in FIGS. 1 and 2. The laser beam 34 is focused on the sample in the capillary 35 by a first lens 36. The divergent light beam from the sample, which is scattered in different directions, for instance $\alpha_1$ and $\alpha_n$, is collimated by a second lens 37 and is then, by a third lens 38, focused on a detector 39 through a pinhole 40. The pinhole 40 determines the volume element of the sample to be monitored. A displaceable diaphragm 41 having at least one pinhole is placed between the lenses 37 and 38 which makes it confocal. This makes it possible to make a measurement of the laser light scattered at different angles by moving the displaceable pinhole diaphragm. The size of the diaphragm determines the space angle of the scattered beam outgoing from the monitored sample, i.e. the coherence area.

Figure 4A:
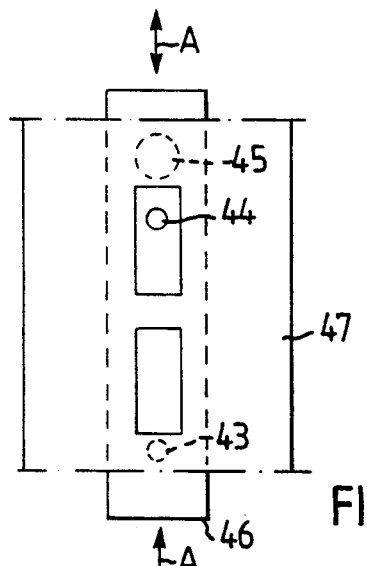
FIG. 4A, 4B, 4C shows an embodiment of a displacable diaphragm device in the embodiment of the instrument according to the invention shown in FIG. 3.
Figure 4B:
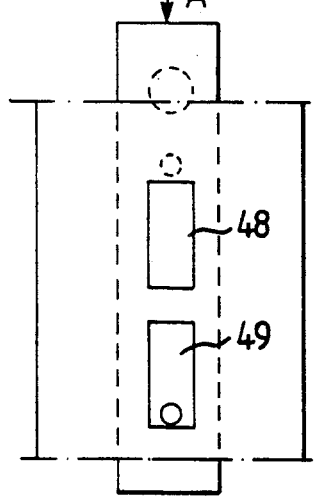
Figure 4C:
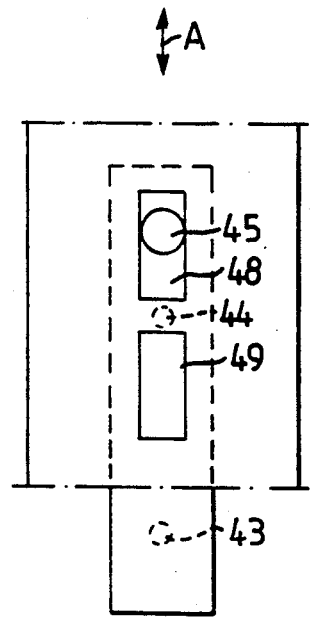

An embodiment of the diaphragm device having a displaceable diaphragm is shown in different positions in FIGS. 4A, 4B and 4C. The non-coherent light scattering must be measured in order to obtain information of the number N of moving sperms in the sample, as will be further explained below. This measurement is made by having a diaphragm of such a size that the number of coherence areas is very great. However, the diaphragm device is also used for the mobility measurements of the spermatozoa, which requires measurement on scattered, coherent light. Therefore the displaceable, confocal diaphragm device is made such that coherent as well as non-coherent scattered light can be measured for different angles by a combination of small (for coherent light) and large (for non-coherent light) apertures 43, 44, 45 provided on an aperture device 46 displaceable in the direction of the arrow A and a stationary mask device 47 placed in front or behind the aperture device. The mask device has large apertures 48 and 49 having such positions and sizes that only one diaphragm aperture 43, 44 or 45 can be provided for the light from the sample at a time for the angle for which measurements are to be made. The apertures 43 and 44 are pinholes providing coherent light and the aperture 45 has a size giving non-coherent scattered light.

According to a second embodiment of the invention shown in FIG. 5 a stationary diaphragm 50 is provided having a pinhole 51 placed on the optical axis of two lenses 52 and 53 placed on each side of it. The lens 52 focuses the image of the sample at the pinhole 51. The pinhole 51 is the volume determining element. The lens 53 has the pinhole 51 in its focal plane such that it collimates the beam from the pinhole. The collimated beam impinges on an array of light detectors D1 to Dn. Even though a row of light detectors is shown it is apparent that the detector array may be composed by detectors only, provided at the places struck by the light scattered in the actual angular directions to be checked, i.e. preferably 2° and 30°. A displaceable detector may be used instead of the array of several detectors (not shown). The detector area may be of a size in itself acting as a pinhole or a pinhole diaphragm may be seated in front of the detector (not shown). The coherence area is determined at the detectors in the embodiment shown in FIG. 5.

In the third embodiment of the invention shown in FIG. 6 the impingement direction of the laser towards the sample is varied instead of the outgoing beam from the sample. The laser, beam 55 impinges on a planar mirror 56 placed at 45° to the impinging beam 55 and being displaceable in the direction of the impinging beam. i.e. in the direction of the arrow B. The mirror 56 is shown in two different positions. A lens 57 is placed in front of the sample in a capillary 58 having its focus in the sample. A lens 59 projects an image of the sample on a pinhole diaphragm 61 placed a distance away in front of a detector 60 such that only the outgoing beam from the sample along the optical axis of the lens 59 and the pinhole 61 reaches the detector 60. A diaphragm 62 determining the coherence area is provided between the lens 59 and the diaphragm 61.

The coherent scattering of light by the sample at different angles in a plane including the capillary or in a plane perpendicular to it is thus measured in order to separate the translation speed v from the rotational frequency f. The angles are chosen as discussed in the articles mentioned above and incorporated herein by reference. Absolute values for v and f are obtained by a non-linear parameterisation of the measured autocorrelation function according to fixed speed distribution functions, because v and f are mean values of a Maxwell-Boltsmann distribution or by parameterisation of the distribution functions for v and f, i.e. p(v) and p(f), using different algorithms.

The absolute number N of movable sperms in a defined volume element can be determined from the amplitude of the autocorrelation function for the non-coherent scattering. This can be made by using the aperture 45 in the aperture device shown in FIGS. 4A to 4C. It is to be observed that each diaphragm determining the coherence area may be exchangeable to have an area only covering about one coherence area or a great number of coherence areas.

In order to be able to make measurements on a large scale a method must be used which permits catching of sperms in seminal liquid in another simple way easy to handle. The capillary 4 shown in FIGS. 1 and 2 can be used for this purpose. The capillary is a tube preferably having a diameter of approximately 1 mm. The sperm liquid is sucked into the capillary. Thereafter the bottom of the capillary is sealed by a plug of for instance wax of an appropriate type for the purpose. The capillary is then placed in a glass cylinder having a substantially larger diameter than the capillary and filled with a liquid as described above. The liquid is kept at a constant temperature by the thermostatic arrangement.

While the designs of instrument herein described constitute preferred embodiments of this invention, it is to be understood that the invention is not limited to these precise designs of instrument, and that changes may be made therein without departing from the scope of the invention.

We claim:

1. Fertility analyzer, comprising
    a) means for emitting a laser beam adapted to impinge on a sperm sample in a capillary having a substantially circular section,
    b) a first optical means including at least a first lens means focusing said laser beam in said sample,
    c) a second optical means including at least a second lens means, a first diaphragm means determining the area of said sample to be monitored, a second diaphragm means determining the space angle of the scattered light from said sample, and a light intensity detecting means,
    d) a separating means included in the combination of said first and second optical means for sorting out a determinable small section of said beam outgoing from said sperm sample in a direction lying in a plane having space symmetry in relation to said capillary, and being displaceable to at least two predetermined positions along a straight path of movement in order to sort out said beam in one direction at a time, and
    e) a signal processing device storing the varying signals from said light detecting means during a predetermined time separately for beams outgoing from said sperm sample in at least two chosen directions, one said beam in one direction at a time, and for computing at least two parameters related to the fertility of the sperm sample.

2. Analyzer according to claim 1, wherein said separating means includes said second lens means which is divided in a first part providing a collimated light beam and a second part providing said focusing of the beam on said detecting means and said second diaphragm means is provided in said collimated light beam between the first and second part of said second lens means and having a diaphragm opening disposable along a line lying in said plane, and said light detecting means includes a detector element placed on the optical axis of said second lens means.

3. Analyzer according to claim 2, wherein said second diaphragm means includes one disposable part having several diaphragm openings provided along its disposal direction and one stationary part having openings adapted to said diaphragm openings such that it for every chosable position of said first part all diaphragm openings except one are covered for the beam outgoing from said sperm sample.

4. Analyzer according to claim 1, wherein said separating means includes said second lens means which is divided in a first and a second part, said first part providing an image of said sample between said first and said second part and wherein said first diaphragm means has its diaphragm opening provided at said image, and said light detecting means includes an array of detector elements provided along a line parallel to said capillary, each detector element providing said second diaphragm for itself.

5. Analyzer according to claim 1, wherein said separating means includes a mirror in said first optical means provided oblique to the beam path of the beam coming from said laser and disposing the beam path impinging an said first lens means parallel to the optical axis of said first lens means along a line parallel to said capillary, and wherein said light detecting means is a single detector element and said first and second diaphragm means in said second optical means are diaphragm openings disposed between the second lens means and said detector element.

6. Analyser according to claim 1, characterized in a cup formed means of glass containing a liquid thermo regulated to a predetermined temperature and having approximately the same refractive index as the capillary at said temperature, into which cup formed means the capillary is seated.

7. Analyzer according to claim 1, wherein that said light detecting means includes at least one one-photone detector.

8. Analyzer according to claim 1, wherein at least one diaphragm opening in said diaphragm means is a pinhole diaphragm having a size transmitting approximately one coherence area of said laser beam.

9. Analyzer according to claim 8, wherein at least one opening in said second diaphragm means is arrangeable to have a size transmitting a substantial number of coherence areas, and in that said signal processing device is adapted to compute the number of sperms per unit of volume by aid of autocorrelation of a series signal samples recorded during a predetermined time having said large sized diaphragm area in a predetermined position.

10. Analyzer according to claim 1, wherein said signal processing device controls said separating means in accordance with a measuring program to automatically in a prescribed order provide prechosen space areas of said beam outgoing from said sperm sample for recording of signal samples during prescribed times.

* * * * *